United States Patent

Alving et al.

(10) Patent No.: US 6,723,056 B1
(45) Date of Patent: Apr. 20, 2004

(54) DEVICE FOR THE COLLECTION, STORAGE AND/OR TRANSPORT OF GAS SAMPLES

(75) Inventors: Kjell Alving, Uppsala (SE); Lars Erik Gustafsson, Hässelby (SE); Jon Lundberg, Stockholm (SE); Eddie Weitzberg, Stockholm (SE)

(73) Assignee: Aerocrine AB (SE)

( * ) Notice: Subject to any disclaimer, the term of this patent is extended or adjusted under 35 U.S.C. 154(b) by 148 days.

(21) Appl. No.: 09/688,860

(22) Filed: Oct. 17, 2000

Related U.S. Application Data (63) Continuation of application No. PCT/SE99/00711, filed on Apr. 29, 1999.

(30) Foreign Application Priority Data

Apr. 30, 1998 (SE) .................................................. 9801532

(51) Int. Cl.⁷ ................................................ A61B 5/00
(52) U.S. Cl. ..................................... 600/543; 600/532
(58) Field of Search ................................. 600/531, 532, 600/543; 73/23.3; 422/84

(56) References Cited

U.S. PATENT DOCUMENTS

| | | | |
|---|---|---|---|
| 3,618,394 A | 11/1971 | Penton | |
| 4,248,245 A * | 2/1981 | Kempin | 600/543 |
| 4,297,871 A * | 11/1981 | Wright et al. | 600/543 |
| 4,947,861 A | 8/1990 | Hamilton | |
| 5,465,728 A * | 11/1995 | Phillips | 600/543 |
| 5,573,005 A | 11/1996 | Ueda et al. | |
| 6,010,459 A * | 1/2000 | Silkoff et al. | 600/532 |
| 6,038,913 A * | 3/2000 | Gustafsson et al. | 600/531 |
| 6,053,874 A * | 4/2000 | Kharitonov et al. | 600/543 |

FOREIGN PATENT DOCUMENTS

| | | |
|---|---|---|
| EP | 559 929 A1 | 3/1992 |
| WO | 90/09572 | 8/1990 |
| WO | 92/05738 | 4/1992 |
| WO | 97/38307 | 10/1997 |

* cited by examiner

Primary Examiner—Robert L. Nasser
(74) Attorney, Agent, or Firm—Banner & Witcoff, Ltd.

(57) ABSTRACT

A gas sample containing an inorganic constituent, such as a sample of exhaled air is collected in a bag (b 1) comprising an inlet/outlet (2) and a reagent chamber (3) which makes possible the storage and transport of said sample and thus enables efficient and repeatable off-line determinations of inorganic components in said sample. A sample collection device, a system comprising said device and a method of its use is disclosed.

6 Claims, 6 Drawing Sheets

DEVICE FOR THE COLLECTION, STORAGE AND/OR TRANSPORT OF GAS SAMPLES

This application is a continuation of international application number PCT/SE99/00711, filed Apr. 29, 1998 pending (status, abandoned, pending, etc.).

The present invention concerns the off-line measurement of components in gas samples taken from the human body, for example exhaled air and in particular samples containing nitric oxide and a system for the collection, storage and/or transport of said samples.

BACKGROUND OF THE INVENTION

That exhaled air contains a complex mixture of gases was observed long ago but the understanding of the clinical importance of these gases is still increasing. For example nitric oxide has been identified as a marker of inflammation in the airways. Further, certain volatile organic compounds have been linked to metabolic disorders, ammonia has been linked to gastric disorders and carbon dioxide is a well known marker of the gas-exchange function of the lungs.

It has inter alia been shown that the level of nitric oxide (NO) in exhaled air of a human subject is indicative of certain disorders (diseases) including risks for acquiring them. This concept has been shown useful at least for the diagnosis of inflammatory conditions of the airways, such as allergic asthma and rhinitis, and respiratory tract infections in humans, and Kartagener's syndrome. In particular infections in the lower respiratory tract may be diagnosed. Systems for the determination of NO levels in exhaled air and diagnostic methods for disorders related to abnormal NO levels have been disclosed in earlier patent applications by the present inventors, for example WO 95/02181 (Kjell Alving et al.) and WO 93/05709 (Lars E. Gustafsson).

The principle of analysing human gas samples, such as samples of exhaled air or gases taken from body cavities, such as from the lumen of the intestines offers many advantages, such as ease and speed. The collection of the samples is non-invasive, painless and thus suitable for both infants and sensitive or weakened patients. Hitherto, the known methods have almost exclusively involved on-line measurements, i.e. the air sample has been directly led or aspired to the inlet of a gas analyzer. When the gaseous component to be determined is nitric oxide, a suitable analyzer is for example a chemiluminescence system (e.g. the Sievers Model 280 Nitric Oxide Analyzer NOA™).

In some cases, exhaled air has been sampled in an intermediate container, such as a syringe, and within a short period of time, injected into the analyser. It has also been attempted to collect air samples in simple balloon-like containers, such as metal coated Mylar® balloons. However, the stability of the sample remains poor, as components of the gas sample, such as a sample of exhaled air undergo various chemical reactions during storage.

In a specific application, that is the measurement of volatile organic material in breath samples and in particular ethanol in alveolar breath, different solutions have been suggested:

U.S. Pat. No. 3,618,394 discloses a method and device for storage and preservation of organic gases having a volatile organic constituent capable of being degraded by the action of micro-organisms. According to one embodiment, a container consisting of a length of indium tubing pinched off at both ends is used. According to another embodiment, a container is coated on the inside walls with an anti-microbial agent.

WO 92/05738 discloses a mouthpiece for an apparatus for detecting the presence of alcohol or drugs in the breath of a user, said mouthpiece including a heating collar to prevent condensation and means to trap the majority of saliva and other contaminants.

The introduction of a system and device for collection, storage and/or transport of human gas samples containing inorganic substances, such as exhaled air samples containing nitric oxide would offer numerous benefits. In hospitals, a central laboratory could perform each analysis, thus eliminating the need of investing in several analysers and also guaranteeing that the analysis is performed each time in a standardised manner. Minor clinics and out-patients could mail samples to a central laboratory. This way, the development of certain diseases indicated by an abnormal or altered level of nitric oxide could be followed or the correct medical dose adjusted without repeated visits to the treating physician.

The problems remaining to be solved comprise the question of how to achieve accurate and repeatable sampling, how to ensure easy and safe handling, and maybe most importantly, the issue of sample stability.

SUMMARY OF THE INVENTION

The present invention eliminates the problems associated with known practices and devices and, additionally, makes possible the economical and efficient off-line measurement of gaseous components-in gas samples, for example exhaled air of mammals, in particular humans. This is achieved by a device comprising at least one inlet/outlet, at least one sample collection compartment and a reagent compartment according to claim 1 and subsequent claims. Further, the inventors disclose an adapter for use with the sample collection device and a system for their use, as specified in the attached claims.

SHORT DESCRIPTION OF THE DRAWINGS

The invention will be described in closer detail in the following description with reference to the enclosed drawings, in which FIGS. 1a, b, c and d show different embodiments of a sample collection device with an internal reagent compartment according to the present invention.

DESCRIPTION

The present inventors disclose a device, system and method which solve the problems associated with known devices and methods. The device, system and method disclosed are not limited to samples of exhaled air, which is used as an example throughout the description. The invention also covers applications where the sample is a sample taken from a body cavity, such as the airways, the bladder and urogential tract, the nasal and/or paranasal sinuses, the gastrointestinal tract or the lumen of the intestines.

Firstly, the stability of the sample and in particular the specific component to be determined has to be guaranteed for a time, sufficient to allow transport and shorter storage of the sample. This can be achieved by eliminating or neutralising unwanted components, either by forcing the exhaled air sample to pass at least one filter or by bringing the sample in contact with reagents, neutralising or absorbing the unwanted components. In the case of gas samples, and in particular samples of exhaled air, in which the nitric oxide content is to be determined, it could be assumed that nitric oxide (NO) is transformed into nitric dioxide ($NO_2$) under the influence of oxygen. Accordingly, the NO content would decrease with time. It has however been shown that the exhaled air's content of carbon dioxide and water influences the stability of nitric oxide in the sample. Particulate matter, water droplets containing bacteria may also influence the stability of NO. Tests performed by the inventors have shown that the level of NO surprisingly increases with time. The term "unwanted components" above should in this context be understood as any component interfering with the NO signal or components compromising the stability of the sample during storage. When the sample is to be subjected to the determination of another component, other than NO, the meaning of the term "unwanted components" is adjusted accordingly.

In order to remove particles and reduce the amount of moisture, the exhaled air may be forced to pass at least one filter, such as a particulate filter, for example a HEPA-type filter. In order to neutralise the carbon dioxide content of the exhaled air, different reagents can be brought in contact with the sample. Suitable hygroscopic and basic compounds can be chosen. Examples of such compounds include, but are not limited to NaOH, KOH; $Mg(OH)_2$, $NaHCO_3$, and $K_3PO_4xH_2O$.

Another approach to the issue of removal or neutralisation of unwanted components is the use of selectively permeable or absorbing materials. The exhaled air sample may for example be forced to pass through a tube, selectively permeable for specific components. One embodiment may comprise a length of tubing, a resistance in the far end of the tubing and a sample collection compartment. When passing through the tubing under a slight pressure, the unwanted components are either absorbed in the walls of the tubing or pass through said walls. Conversely, the component to be determined may pass through the walls and be collected in a sample compartment surrounding the tubing. According to one related embodiment, a gas sample, for example a sample of air is exhaled into a sample collection device consisting of two sample collection bags, whereof the inner one of which is permeable to the component of interest but non-permeable to unwanted components. The inner bag is inflated with the gas sample, for example exhaled air. After a period of time, sufficient for the compound of interest to migrate through the wall of the inner bag, said inner bag is removed from said outer bag without permitting the entry of ambient air in the system and said outer bag sealed. The inner bag may for example be a dialysis membrane, permeable to gases but not to water.

In this context, it is important to note that the sample collection device and in particular the surfaces in prolonged contact with the sample must be chemically inert and chosen so that no unwanted interactions between the gas sample and the surfaces take place. Further, according to specific embodiments, the material should allow heat sealing of the sample compartment, separating it from the reagent chamber or the reagent containing part of the device. Suitable materials include, but are not limited to, metallised plastic foils, e.g. Mylar®, sandwiched plastic films, such as materials normally used in bags for infusion liquids and in packaging.

Secondly, the safety of the subject must be considered. For reasons of safety, the above reagents should never be allowed to come in contact with the patient using the device. Accidental inhalation of reagents must be prevented by the design of the device, through built in security elements, such as one-way valves, filters or the like. In some cases, it is also desirable to limit the time of contact between the sample and the reagent/s. In order to limit the time of contact between the sample and the reagent, it is suggested by the present inventors, that the reagent containing distal end of the sample bag is separated from the proximal end, i.e. the end closer to an inlet. This separation can be achieved by heat sealing the bag or closing it through mechanical means, such as by clamping or similar means. It is also contemplated by the present inventors that the reagent chamber or the reagent containing part, after heat sealing, is physically detached from the sample collection device and discarded.

Alternatively, the reagent/s may be separated from the gas sample by a gas permeable membrane, preferably a membrane selectively permeable to assist in separating the unwanted components from those to be determined. Membranes that are selectively permeable to various gaseous compounds are commercially available for separation of gases and for packaging purposes, e.g. for keeping a controlled atmosphere in packaged food products, fresh meat, fruit and vegetables.

Thirdly, the issue of easy and repeatable handling must be addressed. The sample bag and possible adapters and accessory equipment have to be constructed so, that easy and consistent handling is supported. Construction features and design have to work together to support patient compliance and accurate use. The adapter suggested by the present inventors aims to guarantee that the sample collection device is consistently used, for example by providing a bio-feed back system for controlling the exhalation flow rate.

The present inventors consequently disclose a system for collection, storage and/or transport of gas samples, e.g. air samples, exhaled by a mammal, characterised in that said system comprises: a sample collection device, an adapter having one end capable of being connected to said sample collection device and one end forming an anatomically suitable connection to the mammal, such as a mask or mouthpiece, and a device for diverting a volume of the exhaled air corresponding to the dead space of the mammal delivering the sample.

Said system may further comprise at least one filter for removing unwanted components in the exhaled air. A filter or filters removing particulate matter, bacteria and water aerosols would increase the stability of the sample. A suggested filter is a high efficiency particulate filter, also known as a HEPA filter. The incorporation of filters also has the additional benefit of introducing a certain back pressure or resistance, which facilitates exhaling at an even rate and also closes the soft palate, thus eliminating possible contamination from the nasal airways. Said filter or filters constituting a part of the inventive system may be localised in the adapter or in the inlet to the sample collection device, preferably in the adapter.

Preferably, said system further comprises a device for indicating the exhalation flow rate. Additionally, it is preferred that the device for diverting a volume of the exhaled air corresponding to the dead space of the mammal delivering the sample consists of a nonelastic bag of a volume, corresponding to the dead space volume. This bag can be supplied in a collapsed form, which allows it to expand to its determined volume with little or negligible resistance. It is suggested that these bags are produced in different volumes, corresponding to the dead space of a child, male adult and female adult etc.

It is contemplated, that the adapter could comprise an apparatus for testing pulmonary function or that some characteristics of the adapter above may be integrated in such apparatus.

The present inventors further present a method for the collection, storage and/or transport of air samples exhaled by a mammal, characterised in that said method comprises the following steps: a subject exhales through an adapter into a sample collection device; a reagent or mixture of reagents enclosed in a reagent compartment are brought in contact with the sample of exhaled air; the contact between the sample and the reagent or mixture of regents is interrupted by separating a main portion of the sample volume from the reagent compartment; the sample collection device is transported to the vicinity of a gas analyser; and the sample of exhaled air is delivered to the inlet of a gas analyser, e.g. an equipment capable of detecting and quantifying the components of interest.

Said method may also comprise the determination of another component, other than the main component of interest, i.e. other than the component indicative of a disease or the risk of acquiring a disease. The concentration of this other component may be used as an inner standard, i.e. an indication of the storage time and/or conditions and the result used to compensate for storage dependent variations in the concentration of the main component of interest.

The embodiments of the invention shown in FIGS. 1 through 10 will be explained in closer detail in the following.

Figure 1A:
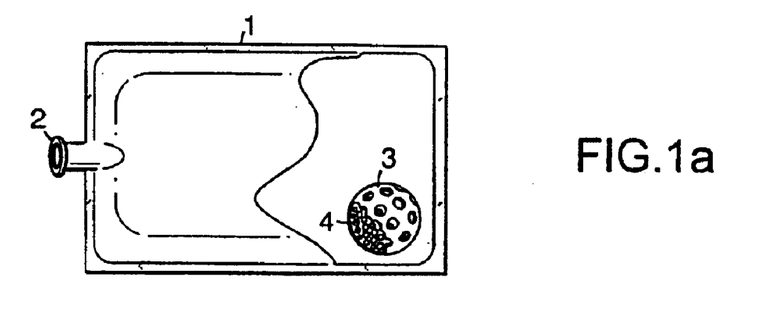

One embodiment shown in FIG. 1a consists of a sample bag 1 having an inlet/outlet 2 and a reagent compartment 3 containing a suitable reagent and/or absorbent 4, for example in the form of granules. In order to ensure proper contact between the gaseous sample and the reagent, the reagent compartment is perforated, the diameter of the perforations being less than the smallest diameter of the granules contained therein. The reagent granules can comprise for example NaOH, KOH, Mg(OH)$_2$, NaHCO$_3$, and K$_3$PO$_4$xH$_2$0 or a mixture thereof.

Figure 1B:
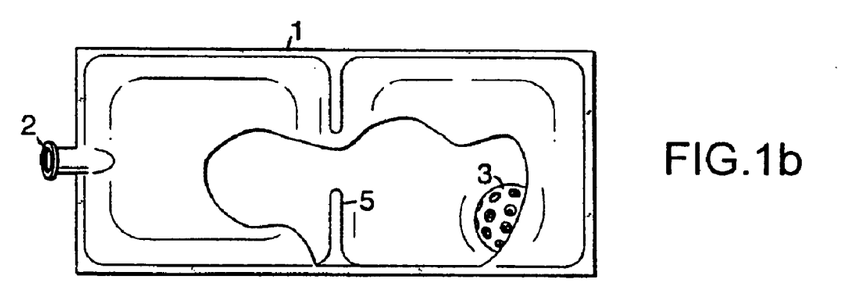

FIG. 1b shows another embodiment, where the sample bag 1 has a constriction 5, enclosing the reagent compartment in the distal part of the bag 1 and preventing it from moving to the vicinity of the inlet/outlet 2. It is conceived, that the distal portion of the bag may be isolated from the proximal portion by closing the constriction e.g. through heat sealing or clamping. The terms distal and proximal are used in this context to denote regions distal to or proximal to the inlet/outlet 2.

Figure 1C:
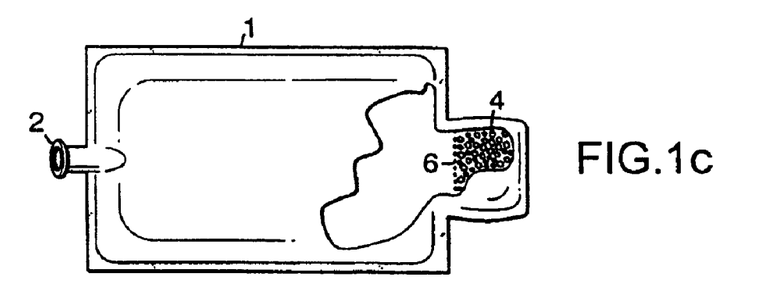

FIG. 1c shows yet another embodiment, where the reagent is enclosed in a part of the sample bag 1, preferably distal to the inlet 2. The reagent mass is separated from the main volume of the sample bag by a membrane or mesh 6, having apertures or a permeability, ensuring proper function of the reagent/absorbent, i.e. the neutralisation or elimination of unwanted components in the sample of exhaled air. This embodiment is well suitable for separation of the reagent containing distal end from the sample containing proximal end of the bag. The terms distal and proximal are again being used in relation to the position of the inlet/outlet.

Figure 1D:
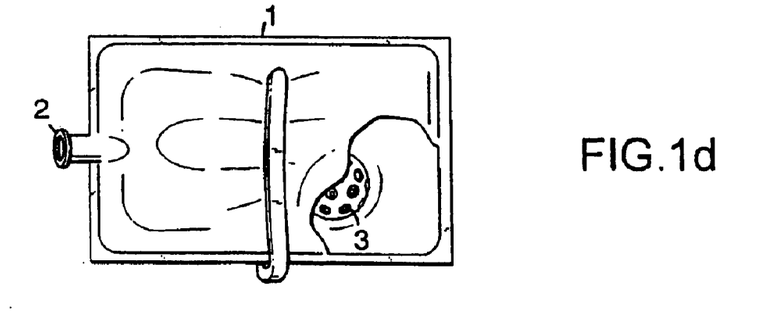

FIG. 1d shows an embodiment, where the distal end of the sample bag 1 containing the reagent compartment 3 is separated from the proximal end by a clamp 7, arranged across the bag.

Figure 2A:
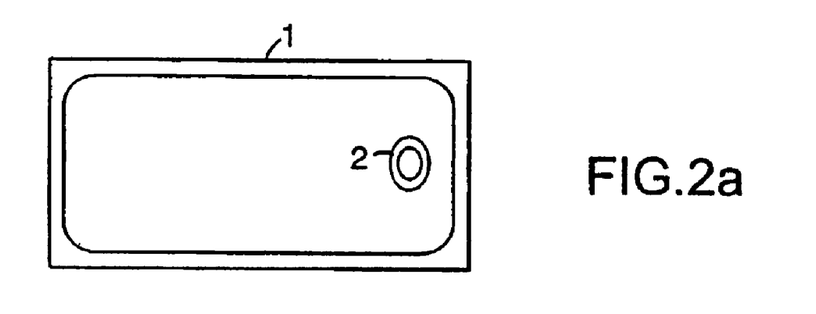
FIGS. 2a, b and c show an embodiment of a sample collection device with an external reagent compartment according to the present invention.
Figure 2B:
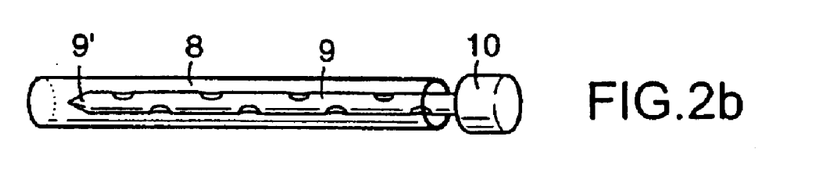
Figure 2C:
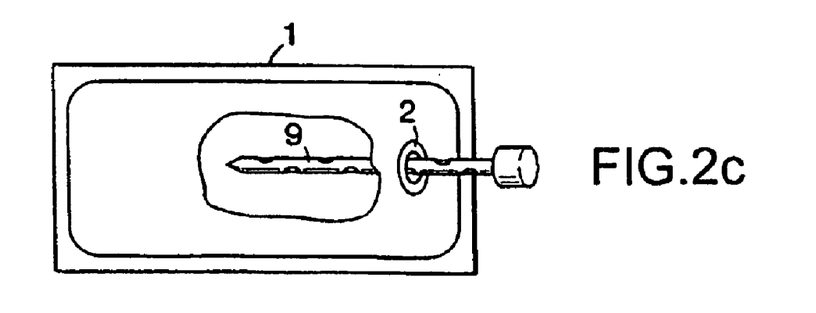

Another approach to the issue of safety and limited time of contact between the sample and the reagents is illustrated in FIGS. 2a, b and c. The reagent and/or absorbent is enclosed in an external element, which may be an oblong element 9 with a sharp end 9', suitable for penetrating the membrane in the inlet/outlet 2. The reagent element 9 is enclosed in a protective, preferably airtight sheath 8, closed by a cap 10. Said cap may also function as an element limiting the length of insertion. The oblong element 9 is preferably a hollow plastic cylinder, enclosing the reagent/absorbent granules, said cylinder having apertures ensuring sufficient contact between the surrounding environment and the reagent granules and also keeping the reagent in place in the cylinder.

Figure 3A:
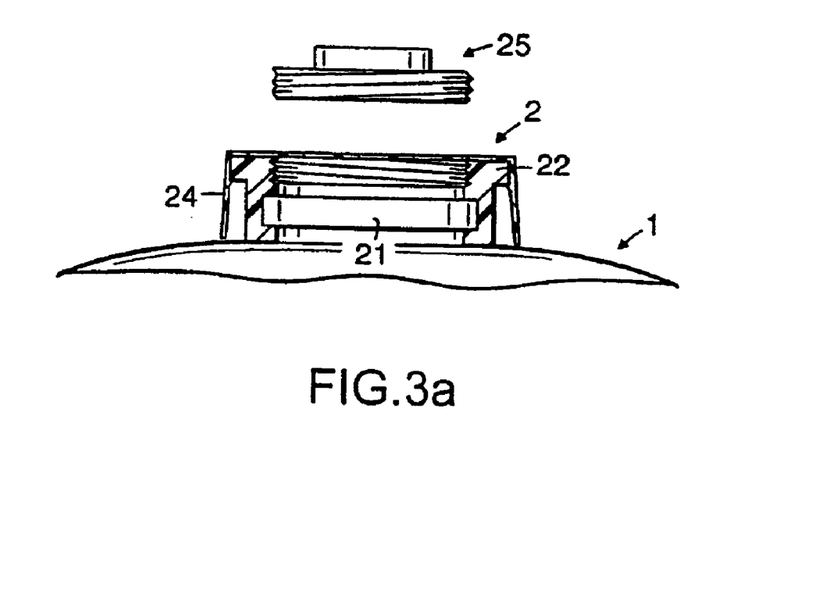
FIGS. 3a and b show detailed views of the inlet/outlet of one embodiment of a sample collection device according to the present invention.
Figure 3B:
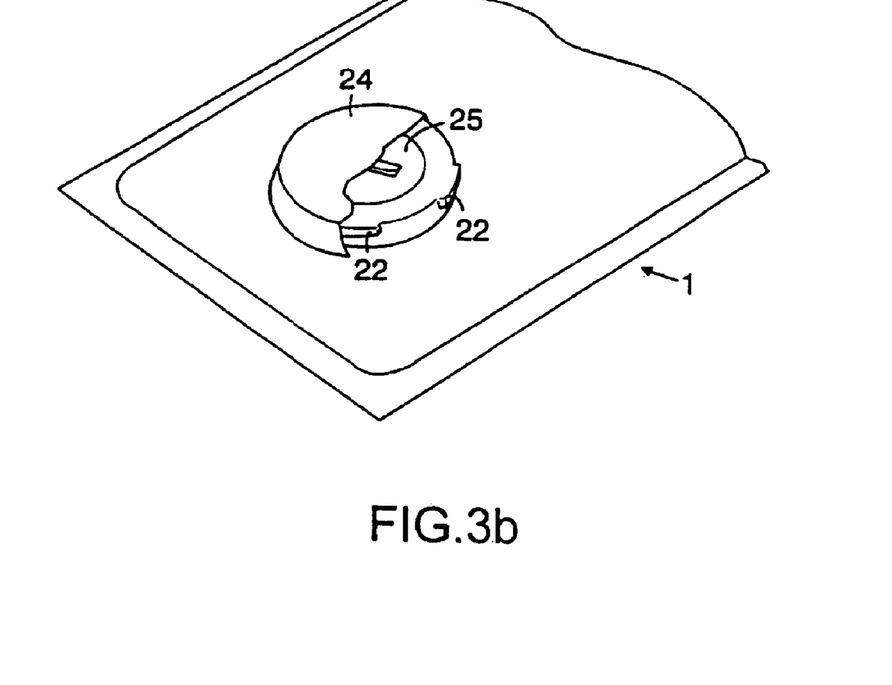

FIGS. 3a and b dwell on the construction of the inlet/outlet 2. Preferably said inlet/outlet is adapted for easy connection to a mouthpiece, an adapter or comparable equipment facilitating the sampling procedure, i.e. the situation when a sample is taken from a patient, for example when a patient exhales into the bag. Likewise, it is preferred that said inlet/outlet is adapted for easy connection to an analyser or for aspiration of a sample for delivery to an analyser. Of course, the bag may be equipped with a separate inlet and outlet. The construction suggested in FIGS. 3a and b only constitutes one embodiment.

FIG. 3a shows a cross section of said inlet/outlet attached to a membrane 11 defining a bag 1, exposing a membrane 21, a locking system such as a bayonet mount 22, inner threads 23, a protective cover 24 and, optionally, a separated, removable threaded plug. The cover 24 and the optional plug 25 ensures the integrity of the membrane during storage and transport. The inner threads 23 are adapted for engaging the plug 25 but may also serve to connect the bag to other equipment, such as a mouthpiece or adapter for the sampling, an analyser or equipment for aspiring the gas and delivering it to an analyser.

FIG. 3b shows a perspective view of the inlet/outlet, with the optional plug engaged and the protective cover in place.

The bag 1 may be one part of a larger system enabling off-line sampling of gases, e.g. including an adapter which may have several functions. It is for example desirable to be able to distinguish between different fractions of the exhaled air, corresponding to the dead space in the airways. It is also desirable that the exhalation is performed with an even flow. The user friendliness is also an important aspect. In order to ensure proper sampling procedures and patient compliance, the adapter should be designed so that it is easy and convenient to use, minimising sources of error etc. An adapter can also function as a housing for filters, removing water vapour and particles (e.g. aerosols and bacteria) from the airflow before it enters the sample bag.

Figure 4:
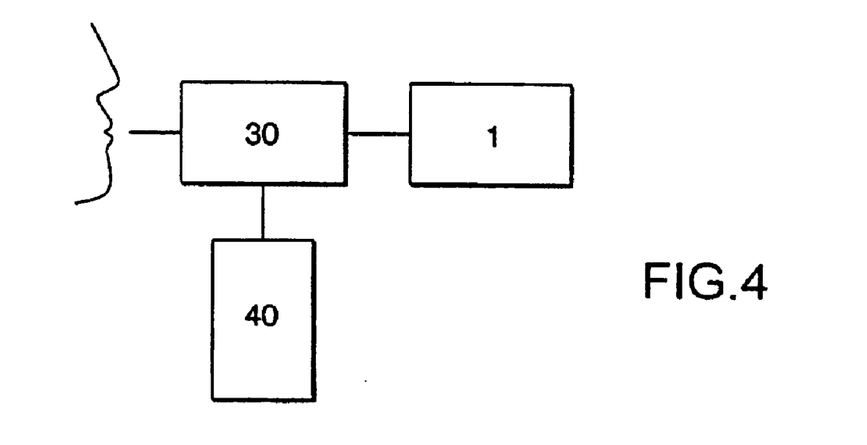
FIG. 4 illustrates the principle of a system for sample collection according to the present invention.

In FIG. 4, a system is schematically presented, comprising a bag 1 for sample collection, an adapter 30 and a device

40 for handling the exhaled volume corresponding to the dead space. The bag 1 can be a bag as described above. The adapter will be presented in closer detail in the following. The device 40 can, in its most simple form, be an airtight, inflatable bag of a known volume, corresponding to the dead space volume. In an other embodiment, the device 40 can comprise flow regulators. In the first phase of the exhalation, the device 40 receives and disposes of a volume corresponding to the dead space volume, where after the exhaled airflow is directed to the sample bag 1. This can be achieved e.g. by arranging a flow resistance in the path leading to the sample bag and providing a second path with a considerably lower resistance, leading to the device 40. When a volume corresponding to the dead space volume has been diverted, the remaining exhalation is directed to the sample bag. This can be achieved by using, as device 40, a bag of a known volume which will expand to said volume with little or negligible resistance, where after the remaining exhalation is forced to enter the sample bag. Alternatively, said device can comprise a valve and flow meter, said valve closing when a predetermined volume has been diverted.

Figure 5:
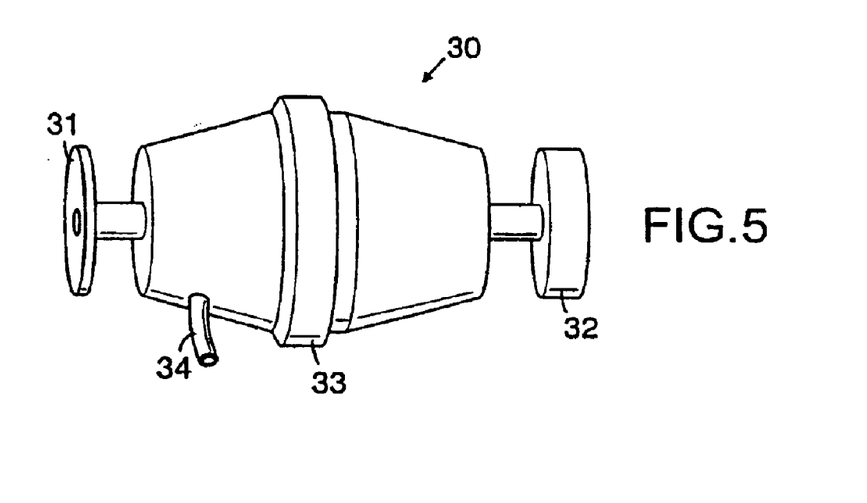
FIG. 5 shows a perspective view of an adapter, suitable for use in the collection of samples of exhaled air.

One further embodiment of an adapter according to the present invention is shown in FIG. 5. The adapter 30 preferably comprises a mouthpiece 31. The term mouth piece in this context may also comprise a device such as a mask, covering both the mouth and nose including provisions for separating exhaled air originating from the upper and lower airways respectively. Further, the adapter has a connective element 32, for example a threaded connection or a bayonet mount, allowing for easy, quick and secure attachment of the adapter 30 to the inlet/outlet 2 of the sample bag 1. Preferably, the adapter 30 is openable, along a division 33, for example a threaded connection between two halves constituting the adapter body. In the described embodiment, the adapter further comprises an outlet 34 for diverting a volume corresponding to the dead space volume of the patient in question. Said outlet can be connected to an inflatable bag as described previously in the description or comprise a flow meter/sensor and a valve.

Figure 6:
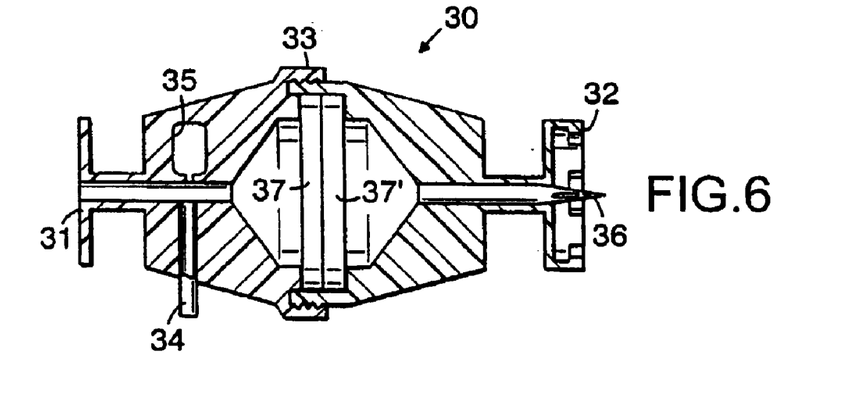
FIG. 6 shows a schematic cross section of the adapter of FIG. 5.

In the cross section of the embodiment of the adapter 30, shown in FIG. 6, further components are presented. The adapter preferably comprises a device 35 for performing at least one of the following functions:

a) creating a positive pressure ensuring the closure of the soft palate and thus eliminating nasal gases, e.g. NO from the measurement;

b) measuring and preferably regulating the air flow, e.g. through a bio-feed back system giving the subject an indication when the desired flow is achieved, alternatively a warning signal when the flow is either too high or too low;

c) diverting a first volume of the exhaled breath, said volume corresponding to the dead space of the person subject to the test, from the main flow and leading this either to a second container 40 or to ambient air.

The device for measuring and preferably also regulating the flow can comprise for example a mechanical valve, with an aperture which changes according to the flow; a valve regulated by a sensor; or a sensor, which through a circuit generates a signal, either an audible signal or a visual signal, prompting the subject to exhale with a constant and optimal flow. Such a sensor can be chosen from commercially available thermal or mechanical sensors, preferably mechanical. Among these, there are commercially available piezoelectric sensors responding to the drag, shear or lift force of the passing air stream. The signal from such a sensor can easily be processed to generate a warning tone or light when the flow deviates from the desired flow.

In the embodiment shown in FIG. 6 a device 36 is shown, which penetrates the membrane 21 in the inlet/outlet 2 and thus makes possible the passage of gas into the bag 1. In FIG. 6 this device is shown as consisting of a hollow needle or cannula but naturally other devices are possible. The important characteristics of a device are that it should allow for easy and secure attachment to the bag 1 and that, upon detachment, bag 1 should be automatically sealed. A cannula penetrating a rubber membrane is one embodiment, fulfilling this requirement.

Further, the adapter 30 may comprise filters, here shown as 37 and 37', indicting that a cassette of two or more filters can be used. Apart from removing moisture, particles and other unwanted components from the air stream, the filter/s also serve to create a positive pressure in the mouth when using the adapter, which pressure forces the subject's soft palate shut, and eliminates nasal NO from entering the bag 1.

Figure 7:
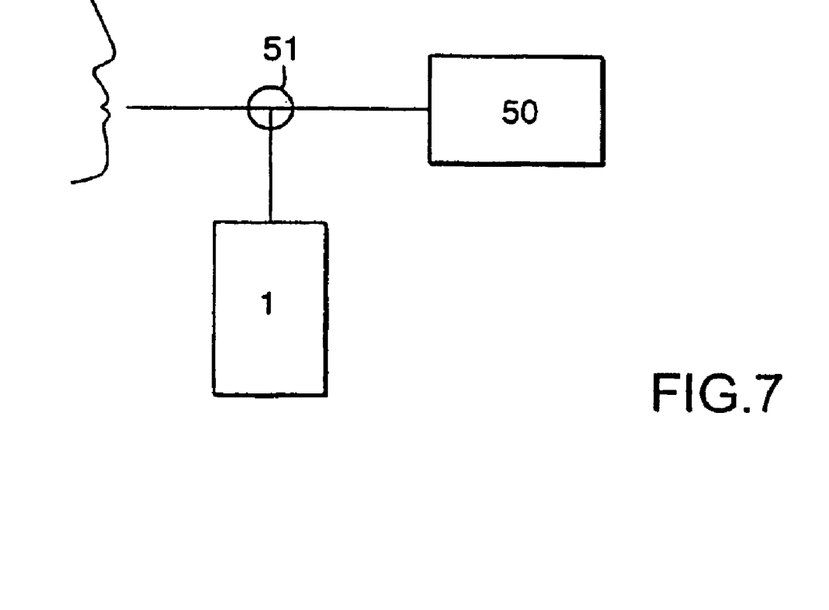
FIG. 7 illustrates the principle of another system for sample collection according to the present invention.

In FIG. 7 a system is schematically shown, where a valve arrangement connects a first container 50 with the mouth piece or mask through which the subject exhales and a sample bag 1 is further connected to the arrangement, through a valve 51 so that a sample can be transferred from the first container 50, to the sample bag 1. According to the present invention, the first container 50 comprises suitable reagents for stabilising the sample air. The subject exhales through the valve 51 and the sample comes in contact with the reagents in the first container 50. After a predetermined period of time has passed, the valve 51 is turned and sample or a portion thereof is transferred to the sample bag 1.

Figure 8:
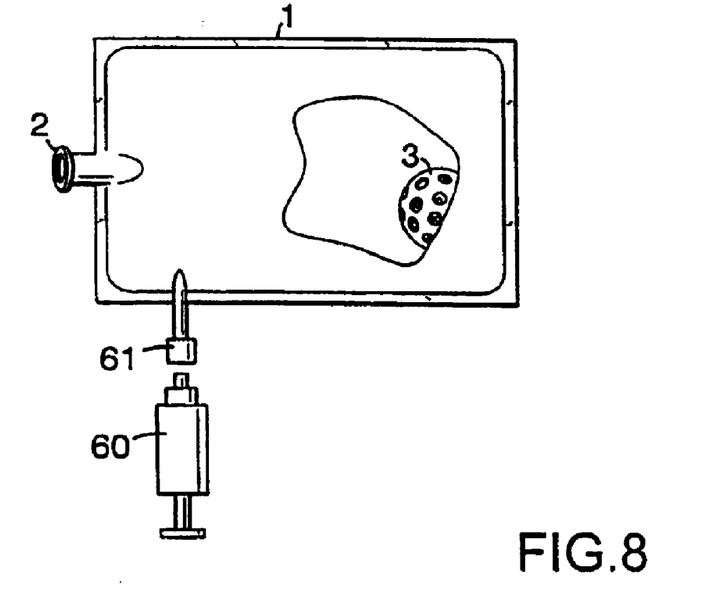
FIG. 8 shows one embodiment of the sample collection device according to the present invention where a sample is aspirated from a first collection device.

One embodiment is shown in FIG. 8, where a sample bag 1, having an inlet/outlet 2 and a reagent container or capsule 3 further has an inlet 61, connectable to a device 60 for aspiration of a sample, e.g. a syringe. In this embodiment, the sample first reacts with the reagents in 3, where after a portion of the sample is extracted from bag 1 to the device 60. The device 60 can naturally be adapted for further storage and transport.

Figure 9:
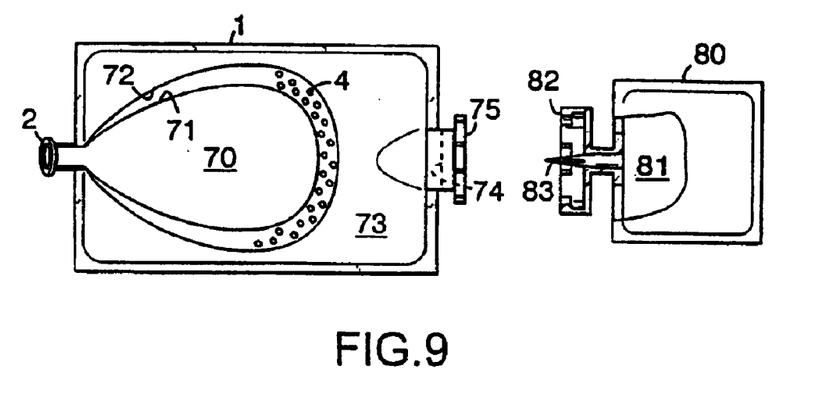
FIG. 9 shows one embodiment of a sample collection device with a two-compartment collection chamber and an external, detachable reagent chamber.

Another embodiment is shown in FIG. 9, where the reagent granules 4 are arranged between two membranes, 71 and 72. The first membrane 71 delimits a first space 70 and the second membrane 72 borders to a second space 73. Said first space 70 is accessed through inlet 2, an inlet corresponding to previously described inlets. Said second space 73 is accessed through a second inlet/outlet 75, connectable to a sample container 80. Said inlet 75 has a membrane 74, which is penetrated by, for example, a hollow needle 83, communicating with a volume 81 in the sample container when the inlet 75 is engaged to engagement means 82 on the container 80.

The described system can be operated as follows: The first inlet 2 is engaged to an adapter 30 or similar device which facilitates the collection of exhaled air in the first space 70. The membranes 71 and 72 being permeable for the desired components to be measured, for example low-molecular weight gases, mainly or only the desired components pass through the reagent layer 4 into the second space 73. The container 80, which may be manufactured in a rigid material, may be evacuated or otherwise constructed so that sample air is aspired from the second space 73 into the space 81, when engaging means 82 are in contact with the inlet 75 and the device 83 has penetrated membrane 74. Said container 80 thus receives a filtered and pretreated sample, suitable for storage and/or transport.

Figure 10:
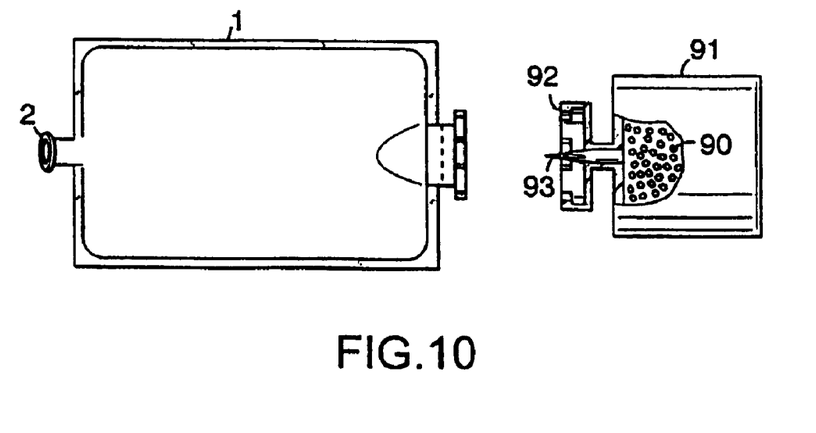
FIG. 10 shows one embodiment of a sample collection device with a one compartment collection chamber and an external, detachable reagent chamber.

Yet another embodiment, shown in FIG. 10, comprises a sample bag 1 with at least one inlet 2 (here shown with two inlets, for reasons of clarity) connectable to a device 90 with a reagent filled space 91. The device 90 has engagement means 92, e.g. a bayonet mount corresponding to the inlet 2 and a device 93, capable of creating a gas passage between sample bag 1 and the reagent containing space 91. The engagement means 92 can further comprise means for automatically releasing the connection after a predetermined time has passed, thereby interrupting the contact between the sample and the reagent/s.

Further embodiments, not illustrated in the drawings, include a device having an inner compartment of an elastic material, connected to an outer compartment by a breakable seal and a cartridge, containing at least one reagent and optional filter. After the subject has filled the inner, elastic compartment with exhaled air, disconnected it from an adapter or mouthpiece and closed the compartment, the breakable seal is opened, forcing the sample to pass from the inner compartment to the outer compartment through the reagent and/or filter cartridge. Preferably, said reagent and/or filter cartridge is further equipped with a one way valve, preventing re-entry of gas from the outer to the inner compartment.

Another embodiment comprises a sample collection device having an inlet equipped with a reagent chamber and optional filters and a one-way valve, preventing accidental contact between the subject and the reagents. This arrangement ensures that all the sample volume passes the filter, if present, and comes in contact with the reagent.

In all embodiments, it is preferred that the sample collection device has provisions for carrying information concerning the time of sampling, the identity of the subject etc. This can be done either by writing or otherwise registering information on specially adapted surfaces on the sample collection device or attaching this information on an adhesive etiquette or by providing the device with at least one surface suitable to write on. Naturally, the information can be provided in electronically readable form, e.g. in the form of bar codes.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

What is claimed is:

1. A hand held device for the collection of gas samples from air exhaled by a human, said gas sample to be measured for NO content, said hand held device comprising a mouth piece, at least one filter, a device adapted to connect to a sample collection device receiving the sample, a device adapted to distinguish between different fractions of the exhaled air, a device adapted to create a positive pressure ensuring the closure of a soft palate, and a device adapted to regulate the air flow rate through the hand held device such that a controlled flow of air passes through the hand held device during exhalation.

2. A hand held device according to claim 1, in which the device adapted to regulate the air flow rate through the hand held device comprises a valve regulated by a sensor.

3. A hand held device according to claim 1, wherein said device adapted to distinguish between different fractions of the exhaled air is capable of diverting a volume of exhaled air corresponding to the dead space volume of the human.

4. A hand held device according to claim 1, in which the hand held device further comprises means for testing pulmonary function.

5. A method for the collection of gas samples from air exhaled by a human comprising the step of: prompting a human to exhale through the hand held device according to claim 1.

6. A method according to claim 5, in which the method further comprises the following steps: removing or neutralizing unwanted components in the sample of exhaled air; and delivering the sample of exhaled air to an equipment capable of detecting and quantifying the amount of NO.

\* \* \* \* \*